(12) United States Patent
Van Der Horst et al.

(10) Patent No.: US 12,220,278 B2
(45) Date of Patent: Feb. 11, 2025

(54) MEDICAL DEVICE COMPRISING SENSOR ARRAY AND SYSTEM FOR MEASUREMENTS

(71) Applicant: KONINKLIJKE PHILIPS N.V., Eindhoven (NL)

(72) Inventors: Arjen Van Der Horst, Tilburg (NL); Roland Alexander Van De Molengraaf, Geldrop (NL); Vincent Adrianus Henneken, Utrecht (NL); Johannes Wilhelmus Weekamp, Beek en Donk (NL); Maarten Petrus Joseph Kuenen, Veldhoven (NL); Sergei Y. Shulepov, Eindhoven (NL); Bruno Jean François Frackowiak, The Hague (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 144 days.

(21) Appl. No.: 17/040,217

(22) PCT Filed: Mar. 11, 2019

(86) PCT No.: PCT/EP2019/055938
§ 371 (c)(1),
(2) Date: Sep. 22, 2020

(87) PCT Pub. No.: WO2019/179795
PCT Pub. Date: Sep. 26, 2019

(65) Prior Publication Data
US 2021/0007711 A1    Jan. 14, 2021

(30) Foreign Application Priority Data
Mar. 23, 2018 (EP) .................................... 18163698

(51) Int. Cl.
*A61B 8/00* (2006.01)
*A61B 8/06* (2006.01)
*A61B 8/12* (2006.01)

(52) U.S. Cl.
CPC .............. *A61B 8/4494* (2013.01); *A61B 8/06* (2013.01); *A61B 8/12* (2013.01)

(58) Field of Classification Search
CPC ........... A61B 8/4494; A61B 8/06; A61B 8/12; A61B 8/445; A61B 8/0891; A61B 8/4488; A61B 8/4483
See application file for complete search history.

(56) References Cited

U.S. PATENT DOCUMENTS 7,192,400 B2    3/2007 Campbell
2005/0121734 A1   6/2005 Degertekin
(Continued)

FOREIGN PATENT DOCUMENTS

EP    2455133 A1    5/2012
WO    2017149421 A1    9/2017

OTHER PUBLICATIONS

International Search Report & Written Opinion of PCT/EP2019/055938, dated Mar. 11, 2019.

*Primary Examiner* — Sean A Frith (57) ABSTRACT

A medical device (10) for insertion into a patient is disclosed. The medical device (10) comprising an elongate body (12), the medical device terminating in a distal portion and further comprising a carrier (20) carrying an annular sensor arrangement (50), wherein the annular sensor arrangement is attached on a forward facing surface of the elongate body (12). Also disclosed is a system (100) including such a medical device (10).

16 Claims, 10 Drawing Sheets

(56) References Cited

U.S. PATENT DOCUMENTS

| | | |
|---|---|---|
| 2007/0016054 A1 | 1/2007 | Cao |
| 2010/0262014 A1* | 10/2010 | Huang .................... A61B 8/12 600/466 |
| 2010/0305451 A1* | 12/2010 | Kim ..................... A61B 5/4839 600/463 |
| 2012/0123270 A1* | 5/2012 | Klee .................... A61B 8/0816 600/453 |
| 2014/0180118 A1* | 6/2014 | Stigall ................. A61B 8/0891 600/463 |
| 2015/0305708 A1* | 10/2015 | Stigall .................... A61B 8/12 600/467 |
| 2015/0335231 A1 | 11/2015 | Van Der Mark |
| 2016/0029999 A1* | 2/2016 | Corl .................... A61B 8/4494 600/463 |
| 2017/0224279 A1 | 8/2017 | Cahan |
| 2017/0265844 A1 | 9/2017 | Nishiwaki |
| 2019/0365348 A1* | 12/2019 | Toume .................. A61B 8/065 |
| 2020/0001121 A1* | 1/2020 | Manbachi ............ A61B 8/0841 |
| 2021/0251599 A1* | 8/2021 | Torp ....................... A61B 8/488 |

\* cited by examiner

MEDICAL DEVICE COMPRISING SENSOR ARRAY AND SYSTEM FOR MEASUREMENTS

CROSS-REFERENCE TO PRIOR APPLICATIONS

This application is the U.S. National Phase application under 35 U.S.C. § 371 of International Application No. PCT/EP2019/055938, filed on Mar. 11, 2019, which claims the benefit of European Patent Application No. 18163698.6, filed on Mar. 23, 2018. These applications are hereby incorporated by reference herein.

FIELD OF THE INVENTION

The present invention relates to a medical device for insertion into a patient, the medical device terminating in a distal portion and comprising an array of sensors.

The present invention further relates to a system comprising such a medical device.

BACKGROUND OF THE INVENTION

In the diagnosis and treatment of cardiovascular disease, minimally invasive medical devices such as catheters and micro-catheters are commonly used to investigate the cardiovascular system of the patient in order to detect anomalies such as for example a stenosis or another deformity within the patient's cardiovascular system. A particularly helpful diagnostic parameter in such investigations is the blood flow velocity within the patient's cardiovascular system as abnormal values of the blood flow velocity provide a strong indication of the presence of an anomaly such as a stenosis or the like in an artery under investigation.

To this end, the minimally invasive medical device may comprise a (central) lumen through which a guidewire may be guided into the patient's artery. It is known to fit the distal tip of such a guidewire with a PZT ultrasound transducer that is operable to perform Doppler ultrasound measurements within the patient's artery from which blood flow velocity-related data can be extracted, such as for example the peak blood flow velocity in the blood vessel under investigation.

Figure 1:
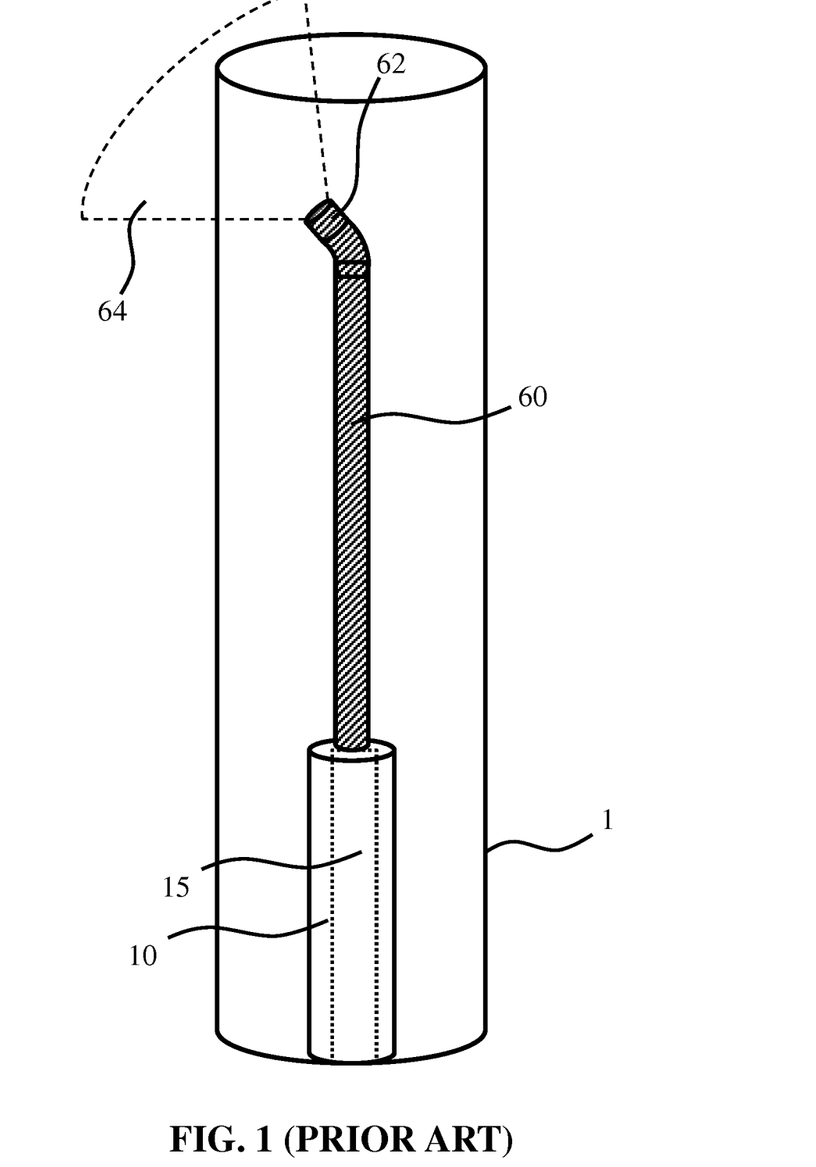
FIG. 1 schematically depicts a cross-sectional view of a prior art minimally invasive medical device inserted into a blood vessel of a patient.

This arrangement is schematically depicted in FIG. 1, in which the medical device 10 is inserted into the blood vessel 1 of the patient, with a guide wire 60 containing the PZT ultrasound transducer 62 at its distal tip being inserted into the blood vessel 1 through a central lumen 15 of the medical device 10. However, as shown in FIG. 1, such procedures are not without problems. More specifically, the guide wire 60 typically is flexible to facilitate the guide wire 60 being guided through the blood vessel 1 of the patient. For this reason, the distal tip of the guide wire 60 does not have a well-defined orientation relative to the blood vessel axis, which can lead to misalignment of the PZT ultrasound transducer 62 with the blood vessel to such an extent that the field of view 64 of the PZT ultrasound transducer 62 predominantly lies outside the blood vessel 1. Consequently, blood flow velocity measurements obtained with the PZT ultrasound transducer 62 at the distal tip of the guide wire 60 can be unreliable, in particular when the field of view 64 of the PZT ultrasound transducer 62 is misaligned with the blood vessel axis.

US 2010/0305451 A1 and EP 2455133 A1 describe medical devices comprising ultrasound transducers at a distal face of the medical device.

It is an objective to improve manufacturability and/or performance of the medical devices.

SUMMARY OF THE INVENTION

The present invention seeks to provide an ambulant medical device for insertion into a patient, e.g. a minimally invasive medical device, which facilitates the reliable determination of blood flow related parameters within the cardiovascular system of the patient.

The present invention further seeks to provide a system for controlling such a medical device.

According to an aspect, there is provided medical device for insertion into a patient, the medical device comprising a lumen body delimiting a lumen, the medical device terminating in a distal portion and further comprising a carrier carrying an annular ultrasound transducer arrangement mounted on a forward facing edge of said lumen body at said distal portion such that the annular ultrasound transducer arrangement is positioned around the lumen.

The present invention is based on the realization that the distal portion of such a medical device, e.g. its distal tip, has a much greater stiffness than for instance a guidewire being fed through its lumen. Also, the guidewire tip is often bent by the medical practitioner prior to an interventional procedure, in order for the medical practitioner to be able to steer the guidewire, the orientation of the (bent) guidewire typically is misaligned with the blood vessel axis. On the other hand, the distal tip of the medical device is better aligned due to this stiffness, which in part may be provided by the presence of part of the guidewire within the section of the lumen in the distal tip. Consequently, the orientation of such a distal portion relative to the axis of the blood vessel in which the medical device is inserted is significantly more stable than the tip of a flexible guidewire being fed through its lumen, such that the orientation of the ultrasound transducer arrangement relative to the blood vessel axis, i.e. the field of view of the ultrasound transducer arrangement, is less prone to variations and associated unreliable blood flow related parameter determinations derived from the data acquired with such an ultrasound transducer arrangement. By orienting the ultrasound transducer arrangement around the lumen exit in the distal portion, objects or fluids may still be passed through the lumen into the cardiovascular system of the patient such that inclusion of the ultrasound transducer arrangement at the distal tip of the medical device according to embodiments of the present invention does not compromise its functionality.

In the context of the present application, the term ultrasound transducer arrangement refers to a collection of ultrasound transducers including at least one ultrasound transducer, such as for example an annular ultrasound transducer aligned with the lumen such that the lumen extends through the annular ultrasound transducer and its carrier.

In some embodiments, the annular ultrasound transducer arrangement comprises a plurality of ultrasound transducers spatially distributed around the lumen. This for example may be advantageous in terms of signal to noise ratio of the acquired ultrasound echoes as a greater number of ultrasound transducers may project a stronger ultrasound beam into the blood vessel into which the medical device is inserted.

In a particular embodiment, the ultrasound transducers are individually addressable. This has the advantage that the shape and direction of the generated ultrasound beam may be electronically steered by individually addressing the respective ultrasound transducers at different points in time and/or in different manners.

The ultrasound transducers may be slanted relative to a central axis of the medical device such that said ultrasound transducers are aiming away from said central axis. This has the advantage that the beam width of the ultrasound beam generated with the ultrasound transducers is increased and that the interference from ultrasound reflections off a guidewire inserted into the field of view of the ultrasound transducers through the lumen is reduced. It may further facilitate the determination of the cross-sectional area of the lumen and, therefore, the absolute flow based on a Doppler spectrum obtained with the ultrasound transducers. In addition, the slant angle offers control over the acoustic performance and beam width of the ultrasound transducer arrangement. For example, a larger slant angle may be used to increase the ultrasound beam width, whereas a smaller slant angle may be used to increase the acoustic signal intensity in a central region of the blood vessel, i.e. around the guidewire.

In a first set of embodiments, the carrier comprises a body mounted on the lumen body of the medical device and a plurality of tapered flexible portions incorporating a silicon island extending from said body, each silicon island comprising at least one ultrasound transducer of the ultrasound transducer arrangement, said tapered flexible islands being folded over said forward facing edge of the lumen body. Such a carrier for example may be realized using so-called flex-to-rigid (F2R) technology in which rigid silicon islands carrying circuit components such as the ultrasound transducers are suspended in a flexible polymer matrix such as a polyimide matrix, which may be multi-layered such that electrical connections to the silicon islands run in between such polymer layers, which are typically made from an electrically insulating polymer such that the electrical connections are electrically insulated from the outside world. With such a flexible arrangement, the carrier may be positioned onto the lumen body of the medical device in a straightforward manner, whilst also facilitating the orientation of the ultrasound transducer under a slanted angle with its central axis as previously described.

In an embodiment, the medical device further comprises a plurality of (electrically conductive) wires extending in a length direction of the medical device over the lumen body, each of said wires being connected to one of said silicon islands. For example, such wires may be connected to the backside of a silicon island, in which case the silicon island for example may comprise one or more through silicon vias that connect the wire to the circuitry, e.g. the ultrasound transducers, at the front side of the silicon island. Alternatively, a wire may be connected to a side surface of such a silicon island onto which a contact may be present for connecting the wire to such circuitry.

Instead of a plurality of silicon islands, the carrier may comprise an annular ring carrying the ultrasound transducer arrangement, e.g. one or more ultrasound transducers. The annular ring may fit around the lumen such that the lumen extends through the annular ring and may be rigid, e.g. a silicon annular ring, which has the advantage of ease of manufacture.

Such a carrier may further comprise at least one contact on the lumen body of the medical device and a flexible connection between the at least one contact and the ultrasound transducer arrangement and a (conductive) wire connected to the at least one contact and extending in a length direction of the medical device over the lumen body. This facilitates the connectivity of the ultrasound transducer arrangement as the one or more contacts may be positioned on the lumen body whilst the flexible connection ensures that the annular ring may be folded over the forward facing edge of the lumen body around the lumen.

Alternatively, the carrier comprises a double-walled housing in which the annular ring is housed, said housing including an outer wall fitted around the lumen body. Such a double-walled housing may comprise an inner wall and an outer wall in between which the ultrasound transducer arrangement is positioned, e.g. in the form of an annular substrate. This is particularly suitable when the ultrasound transducer arrangement comprises one or more PZT (lead zirconate titanate; $(Pb[Zr_{(x)}Ti_{(1-x)}]O_3))$ elements.

In a further set of embodiments, the ultrasound transducer arrangement comprises one or more CMUT (capacitive micromachined ultrasound transducer) elements or PMUT (piezoelectric micromachined ultrasound transducer) elements. The use of CMUT elements is particularly preferred due to their superior acoustic characteristics. Other ultrasound transducer technologies, e.g. single crystal transducers, may also be contemplated.

The medical device may further comprise at least one of a pressure sensor and an imaging element on an outer surface of the distal portion of the medical device proximal to the ultrasound transducer arrangement. This may assist in acquiring further diagnostically relevant information with the medical device.

For example, where the medical device further comprises a pressure sensor, this enables simultaneous determination of blood flow velocity parameters and blood pressure, which may assist the assessment of the resistance associated with localized narrowing of the blood vessel and microcirculation. Moreover, using both blood pressure and velocity information, the pulse wave velocity may be determined, which may be useful for patient stratification for renal denervation.

Where the medical device further comprises an imaging element such as an ultrasound transducer element or an optical element, such an imaging element can provide anatomical information together with blood flow velocity (and blood pressure) measurements. This for example enables the determination of the absolute blood flow rate, which is beneficial in measuring cardiac output for instance.

The medical device according to embodiments of the present invention may be a catheter, preferably a micro-catheter. In the context of the present invention, a micro-catheter is a catheter suitable for insertion into the cardiovascular system of a patient, and may have an outer diameter of less than 1 mm for this reason. The micro-catheter in some embodiments is operable as an infusion catheter, e.g. to infuse vasoactive agents or embolization agents into the patient. This has the advantage that the ultrasound transducer arrangement can be used to monitor the infusion velocity of such agents, thereby improving the accuracy of the infusion process and potentially reducing discomfort to the patient. In case of embolization, such monitoring may be used to detect the occurrence of a backflow of the embolization agent, which provides an accurate signal as to when to stop the embolization procedure.

According to another aspect, there is provided a system comprising the medical device of any of the herein described embodiments and a control unit adapted to control the ultrasound transducer arrangement of the medical device at least in a Doppler ultrasound mode. Such a system may be used to accurately determine blood flow related parameters of a patient whilst the medical device is inserted into a cardiovascular system, e.g. a blood vessel, of the patient.

In an embodiment, the ultrasound transducer arrangement comprises a plurality of individually addressable ultrasound transducer elements, and wherein the control unit is adapted to, for each ultrasound transducer element, determine a peak blood flow velocity from the ultrasound data obtained with said ultrasound transducer element; and electronically steer an ultrasound beam produced by the plurality of individually addressable ultrasound transducer elements based on the determined peak blood flow velocities. By using the respective peak blood flow velocities as determined with the respective ultrasound transducer elements, the alignment of the medical device within the patient's blood vessel can be determined, based on which the operation of the ultrasound transducer arrangement can be optimized using electronic beam steering.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

It should be understood that the Figures are merely schematic and are not drawn to scale. It should also be understood that the same reference numerals are used throughout the Figures to indicate the same or similar parts.

Figure 2:
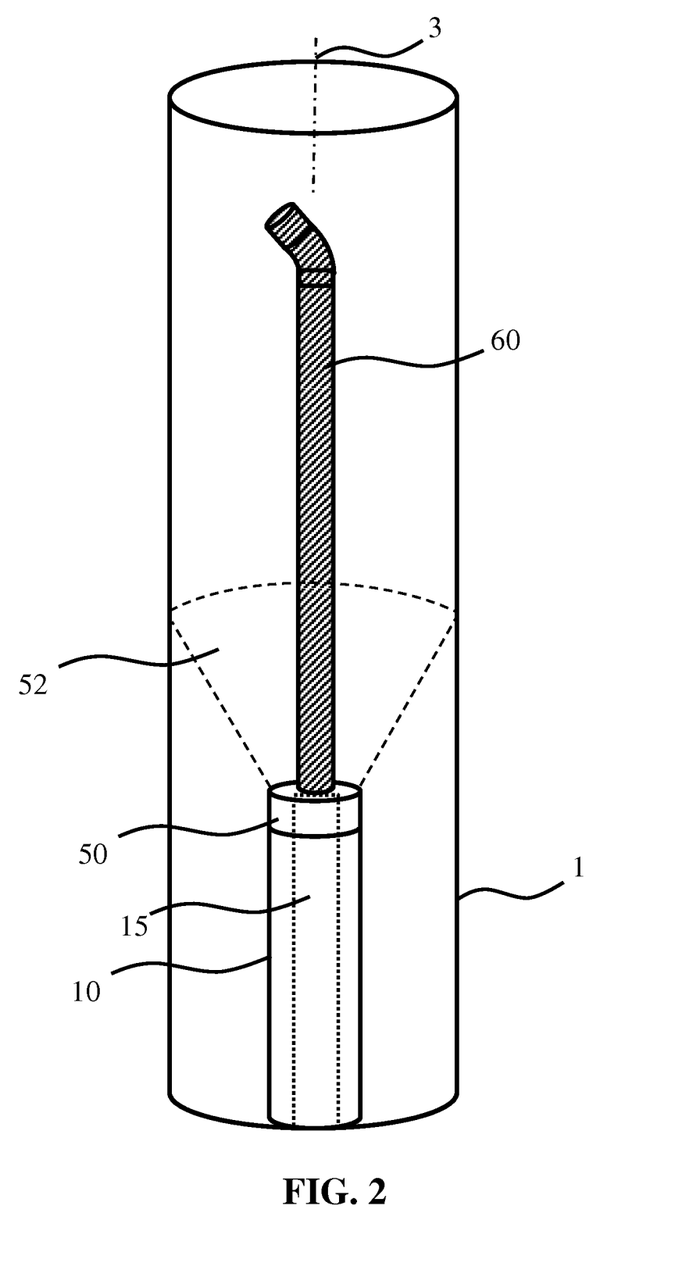
FIG. 2 schematically depicts a cross-sectional view of a minimally invasive medical device according to an example embodiment inserted into a blood vessel of a patient.

FIG. 2 schematically depicts a medical device 10 according to an example embodiment of the present invention in situ within a blood vessel 1 of a patient. The medical device 10 comprises an ultrasound transducer arrangement 50 at its distal tip such that the one or more ultrasound transducers of the ultrasound transducer arrangement 50 are annularly arranged at the distal tip around the central lumen 15 of the medical device 10. The one or more ultrasound transducers typically are forward facing such that the field of view 52 (i.e. the ultrasound beam) of the one or more ultrasound transducers extends into the blood vessel 1 ahead of the medical device 10. Due to the larger stiffness of the body of the medical device 10 compared to an instrument such as a guide wire 60 that may be inserted into the blood vessel 1 of the patient via the central lumen 15 of the medical device 10, the body of the medical device 10 maintains a better alignment with the central axis 3 of the blood vessel 1. As explained above, misalignment of e.g. a guidewire within the blood vessel 1 may be caused by its more flexible nature as well as by pre-bending, whereas the greater stiffness of the distal portion of the medical device 10 in part may be contributed to the presence of part of such a guidewire extending through the lumen 15. Consequently, the field of view 52 substantially is kept within the blood vessel 1 of the patient such that blood flow-related parameters such as (peak) blood flow velocity of the blood flow of the patient through the blood vessel 1, for instance using Doppler ultrasound with the one or more ultrasound transducers of the ultrasound transducer arrangement 50, may be determined more reliably due to the increased stability of the orientation of the medical device 10 relative to the axis 3 of the blood vessel 1.

The medical device 10 may be a catheter and more preferably may be a micro-catheter having one or more lumens 15 through which tools such as a guidewire can be inserted (guided) into the patient. Alternatively, the medical device 10 may be an infusion catheter through which a fluid may be infused into the blood vessel 1 of the patient via the lumen 15 or a separate lumen (not shown). In the latter embodiment, the ultrasound transducer arrangement 50 may be operable in Doppler mode in order to determine flow related parameters of the fluid being infused into the patient, such as flow direction of flow velocity. Such fluids for example may include vasoactive agents or embolization agents as is well-known per se to the skilled person. The flow related parameters of the infused fluid as determined with the ultrasound transducer arrangement 50 may be used to quantify the amount of fluid that has been infused into the patient such that these parameters may be used to determine when the infusion procedure may be terminated. For example, in case of an embolization procedure, the ultrasound transducer arrangement 50 may be used to determine backflow of the embolization agent, which may be used as an indicator to terminate such a procedure.

The ultrasound transducer arrangement 50 may include any suitable type of ultrasound transducers, such as piezoelectric ultrasound transducers or capacitive ultrasound transducers. Examples of piezoelectric ultrasound transducers include PZT elements and PMUT elements whereas examples of capacitive ultrasound transducers include CMUT elements. Other suitable types of ultrasound transducers will be apparent to the skilled person.

In the following, a number of example embodiments of the integration of the ultrasound transducer arrangement 50 onto the medical device 10 will be explained in further detail. However, it should be understood that these examples are not intended to limit the scope of protection for the present invention to these examples only and that alternative examples that will be immediately apparent to the skilled person based on the teachings of the present application are also intended to be covered thereby.

Figure 3:
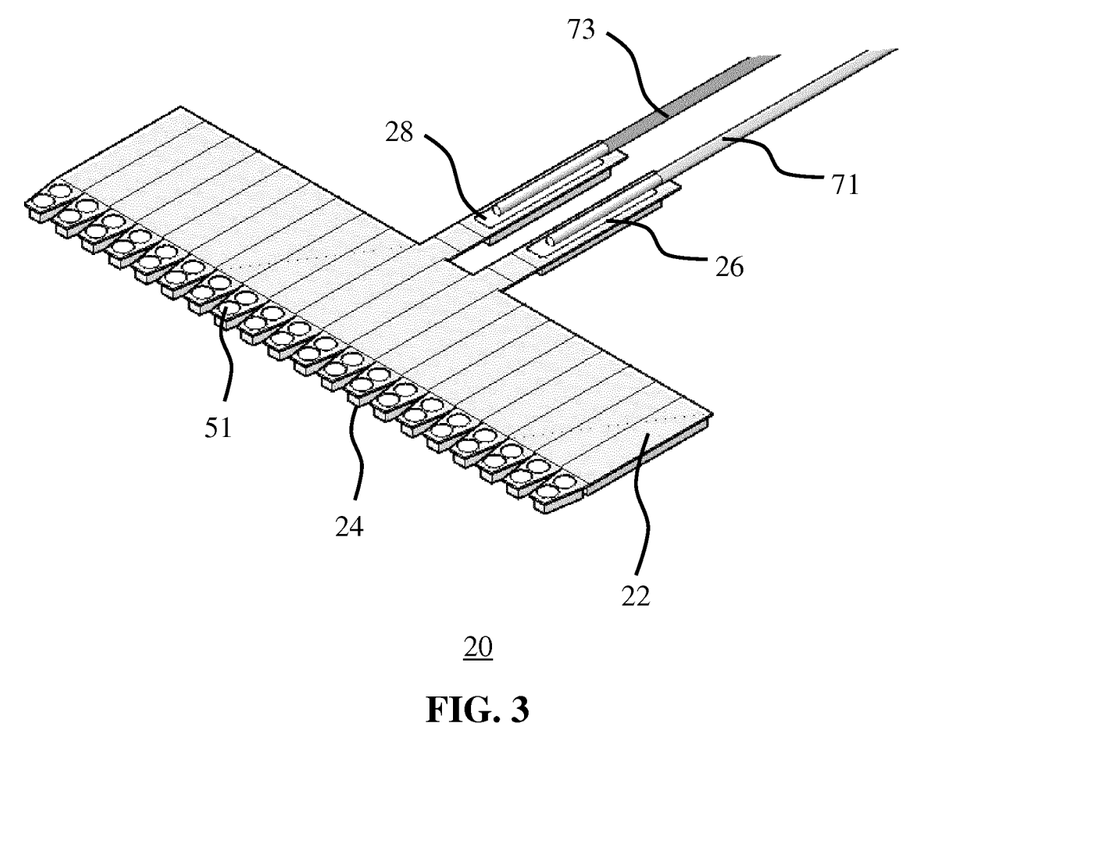
FIG. 3 schematically depicts a top view of a carrier for mounting on a medical device according to an embodiment.
Figure 4:
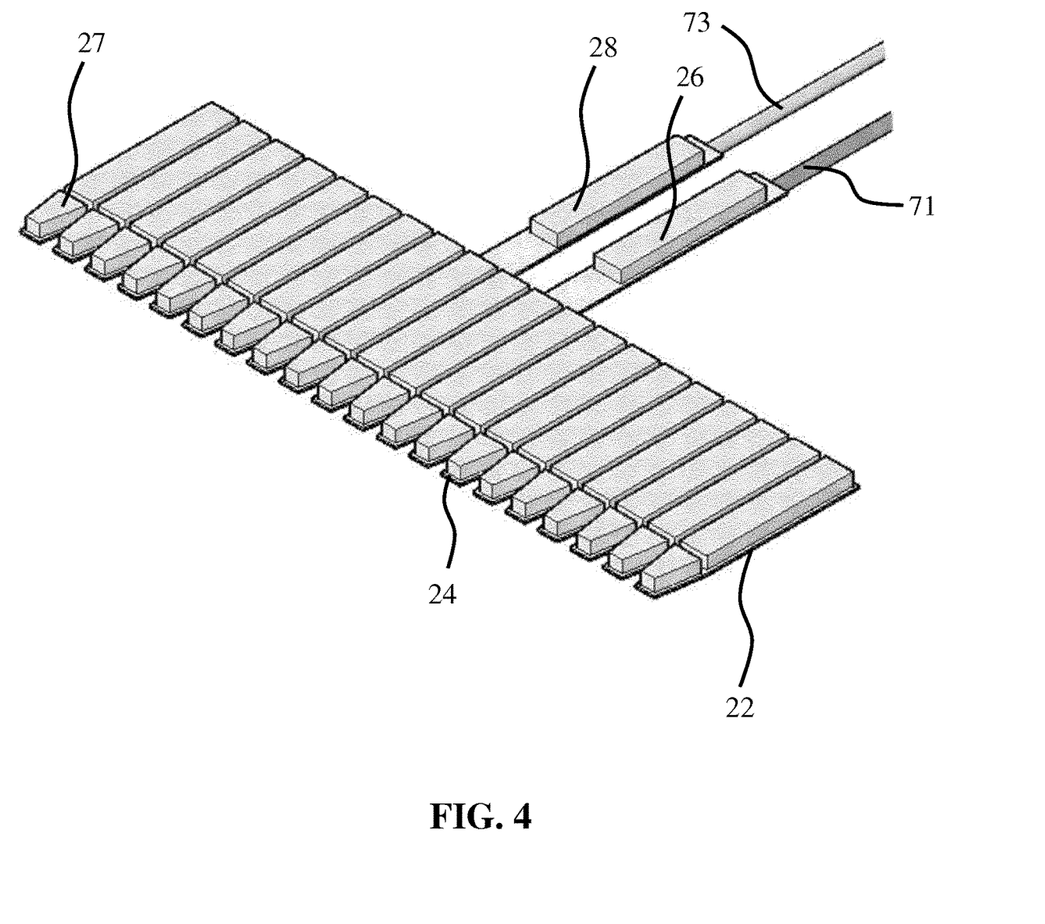
FIG. 4 schematically depicts a bottom view of a carrier for mounting on a medical device according to an embodiment.

In a first set of embodiments, a carrier or assembly 20 is provided using so-called flex-to-rigid technology. FIG. 3 schematically depicts a top view and FIG. 4 schematically depicts a bottom view of such a carrier 20. The carrier 20 comprises a flexible body 22 from which a plurality of fingers 24 extend. As will be explained in further detail below, the fingers 24 taper inwardly in a direction away from the flexible body 22 such that when the body 22 is folded around the inner wall delimiting the central lumen 15 of the medical device 10, the fingers 24 can be folded over the edge of the inner wall, thereby defining an annulus on said edge. Each of the fingers 24 comprises at least one silicon island 27 carrying an ultrasound transducer element 51. In FIG. 3, two such ultrasound transducers 51 are shown on each finger 24 by way of non-limiting example only as it should be understood that any suitable number of such ultrasound transducers 51 may be incorporated on the fingers 24, which will depend on the thickness of the edge of the inner wall over which the fingers 24 are folded as mentioned above.

In an embodiment, the carrier 20 further comprises further silicon islands 26, 28 acting as contacts for the ultrasound transducer elements 51 that extend from the side of the body 22 of the carrier opposite the fingers 24 to which wires 71, 73 may be connected in any suitable manner in order to allow communication between the ultrasound elements 51 and a control unit (not shown), e.g. to control the ultrasound transducer elements 51 and communicate data between the ultrasound transducer elements 51 and the control unit. The contacts 26, 28 are typically connected to the silicon islands 27 carrying the ultrasound transducer elements 51 through conductive tracks, e.g. aluminium tracks, extending through the body 22 of the carrier 20. The body 22 for this purpose may be a multi-layered body comprising at least two electrically insulating polymer layers such as polyimide layers in between which such conductive tracks are formed. It is noted for the avoidance of doubt that two contacts 26, 28 are shown by way of non-limiting example only as the carrier 20 may have any suitable number of such contacts and wires connected thereto.

Alternatively, although not shown in the drawings, the connection wires 71, 73 may extend to the silicon islands 27 carrying the ultrasound transducer elements 51 such that the contacts 26, 28 may be omitted. In such embodiments, the wires 71, 73 may be connected to the backside of such a silicon island 27, with through silicon vias through the silicon islands connecting the wires 71, 73 to the ultrasound transducer elements 51, or to a side surface of such a silicon island where a landing pad or contact for such wires may be present.

The ultrasound transducer elements 51 may be individually controllable or addressable, for example to allow electronic beam steering of the ultrasound beam produced by the ultrasound transducer elements 51. The ultrasound transducer elements 51 may be electrically connected to an Application Specific Integrated Circuit (ASIC) at a nearby position on the medical device 10 for signal conditioning, analog to digital conversion, multiplexing or the like. In an embodiment, the ultrasound transducer elements 51 are CMUT elements although it should be understood that alternatively the ultrasound transducer elements 51 may be PMUT elements or PZT elements.

Figure 5:
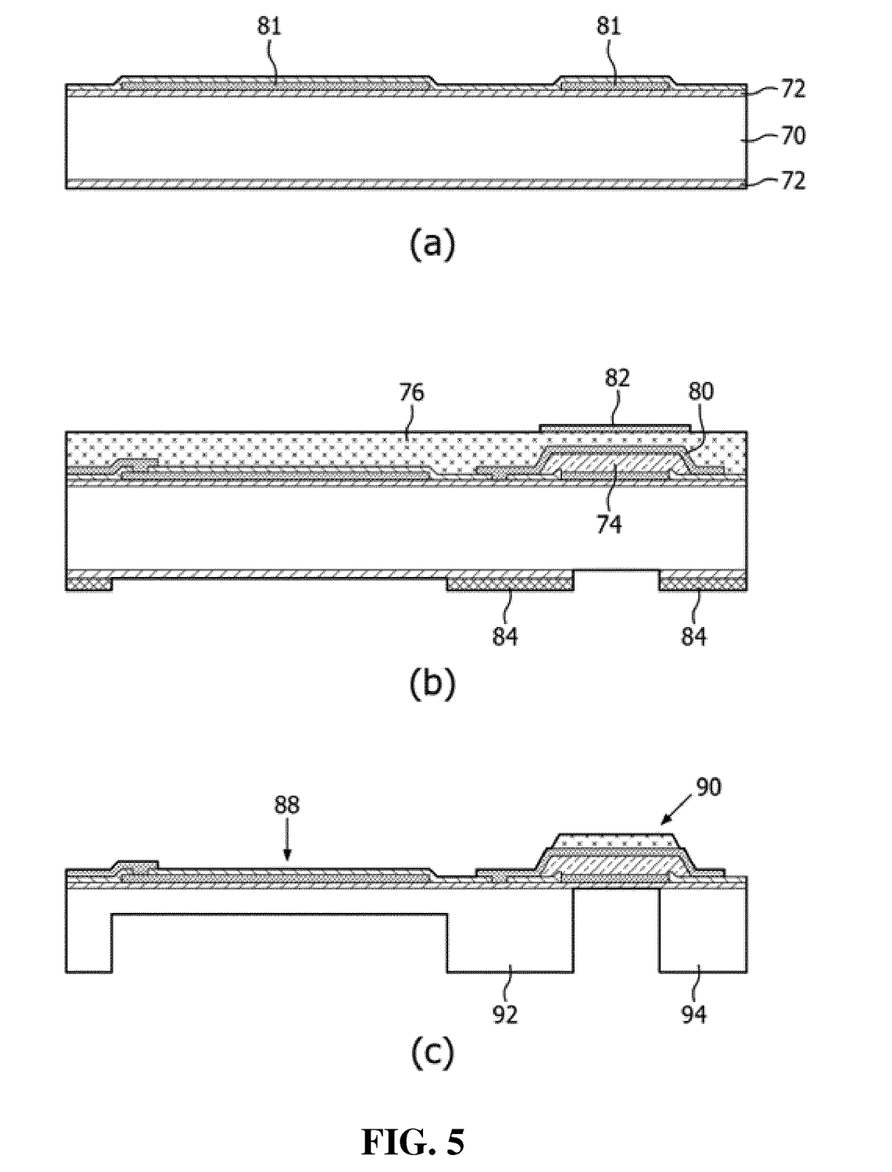
FIG. 5 schematically depicts a flex-to-rigid manufacturing method.

FIG. 5 illustrates several process steps in the formation of a flexible foil bridge joining two silicon islands, e.g. a silicon island 27 on which one or more ultrasound transducer cells 51 are located and a silicon island carrying a contact 26, 28. It should be understood that FIG. 5 provides an example flex-to-rigid process by way of non-limiting example only and that many variations to this example process both in terms of process steps as well as materials used will be immediately apparent to the skilled person such that it should be understood that the embodiments of the medical device 10 in which the ultrasound transducer arrangement 50 is provided using such flex-to-rigid technology is not limited to the shown method and materials.

FIG. 5a) shows a silicon wafer 70 with thermal silicon dioxide layers 72 grown on the top and bottom sides. Patterned aluminium areas 81 are sputtered on the top side and patterned using standard lithography. A patterned area of polyimide 74 is laid over one of the aluminium areas on the top side, which pattern defines the bridges in the flexible foil. In case of a continuous flexible foil, the polyimide 74 may be a continuous sheet. An aluminium layer 80 is deposited over the polyimide 74 and a second polyimide layer 76 is laid over the aluminium. Another layer of aluminium 82 is patterned over the aluminium layer 80 for use as a mask during etching, all as shown in FIG. 5b). Finally, as shown in FIG. 5c), the silicon wafer 70 is etched away from the back in areas outside the masked by thick resist areas 84, both under silicon island location 88 and under the flexible bridge 74, 80, 76. The polyimide layer 76 on either side of the flexible bridge 90 on the top side is patterned away on either side of etch mask layer 82, which is then itself etched away. The result is two separate silicon islands 92 and 94, joined by a flexible bridge 90. The flexible bridge 90 and others like it enable an array of such ultrasound transducer 51 populated islands to be wrapped over the distal tip of the medical device 10 as previously explained.

Figure 6:
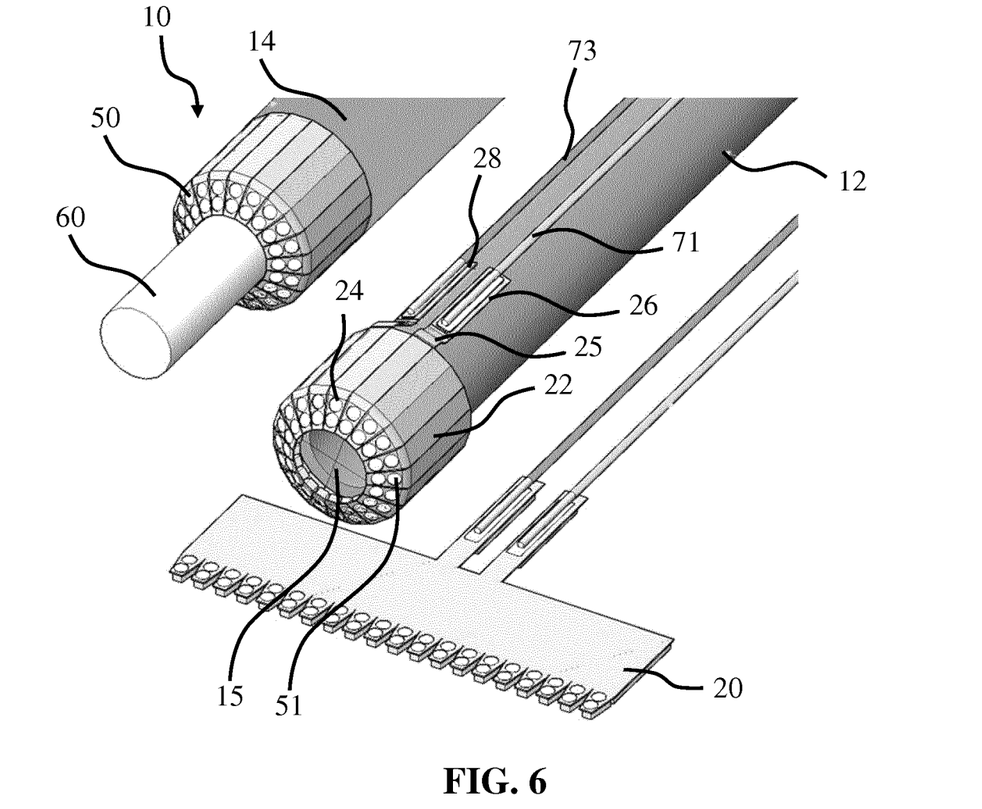
FIG. 6 schematically depicts an assembly method for such a carrier onto a medical device according to an embodiment.

This is shown in more detail in FIG. 6, in which the integration of such a carrier 20 onto the distal portion of the medical device 10 is schematically depicted. As shown in FIG. 6, the flexible body 22 of the carrier 20 is wrapped around the lumen body 12 of the medical device 10 delimiting one or more lumens, e.g. a central lumen 15 such that the contacts 26, 28 (if present) and the wires 71, 73 are positioned on the lumen body 12, with the wires 71, 73 extending along the lumen body 12 in a length direction of the medical device 10. The fingers 24 carrying the one or more ultrasound transducer elements 51 are folded over the forward facing edge of the lumen body 12, thereby forming a forward facing annular ultrasound transducer arrangement 50 around the exit port of the central lumen 15, such that the central lumen 15 extends through this ultrasound transducer arrangement 50, thereby facilitating the use of an instrument such as a guidewire 60 in combination with the ultrasound transducer arrangement 50. The carrier 20 (or at least parts thereof such as the body 22 and/or the fingers 24) may be secured to the lumen body 12 in any suitable manner, e.g. using a biocompatible adhesive. Subsequently, the outer sheath or surface 14 of the medical device 10 may be formed, e.g. through coating or the like, in order to embed the wires 71, 73 and contacts 26, 28 within the medical device 10, i.e. in between the lumen body 12 and the outer surface 14. The lumen body 12 and the outer sheath 14 may be made on any suitable material, e.g. any suitable (biocompatible) polymer or the like.

Figure 7:
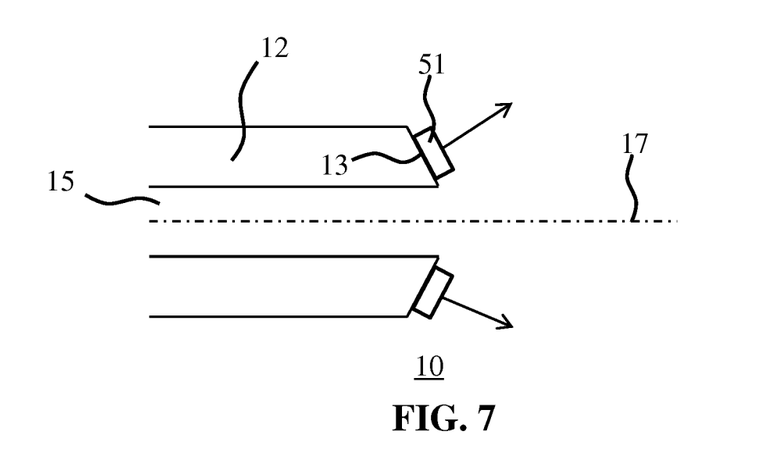
FIG. 7 schematically depicts a cross-sectional view of an aspect of a minimally invasive medical device according to another example embodiment.

FIG. 7 schematically depicts the distal portion of the medical device 10 in cross-sectional view according to an alternative embodiment of the present invention, in which the forward facing edge 13 of the lumen body 12 surrounding the exit port of the lumen 15 is slanted relative to the central axis 17 of the lumen 15 (or the medical device 10) such that the surface normal of this forward facing edge 13 is angled away from this central axis 17. Consequently, the ultrasound transducer elements 51 mounted on the slanted forward facing edge 13 of the lumen body 12, e.g. when on the fingers 24 of the flex-to-rigid carrier 20, are angled away from this central axis 17, that is the central aim of an ultrasound beam generated with the ultrasound transducer arrangement 50 comprising the ultrasound transducer elements 51 is aimed away from the central axis 17.

This slanted orientation of the ultrasound transducer elements 51 has a number of advantages. Firstly, when in situ, an instrument such as a guide wire 60 extending beyond the exit port of the lumen 15 into the blood vessel 1 of a patient is less likely to cause interference with such an ultrasound beam as the instrument due to the ultrasound beam aiming away from such an instrument, at least when it extends into the blood vessel 1 in a more a less straight manner, i.e. along the central axis 17. Secondly, damage of the wall of the blood vessel 1 by the distal tip of the medical device 10 having such a slanted edge 13 is less likely, whilst thirdly it facilitates determination of the cross-sectional area of the lumen 15, from which the absolute blood flow can be derived using the Doppler spectrum obtained with the ultrasound transducer arrangement 50. As previously mentioned, the slant angle offers control over the acoustic performance and beam width of the ultrasound transducer arrangement. For example, a larger slant angle may be used to increase the ultrasound beam width, whereas a smaller slant angle may be used to increase the acoustic signal intensity in a central region of the blood vessel, i.e. around the guidewire.

It is further noted that the slant angle of the ultrasound transducer 51 is not necessarily the same as the external slant angle of the medical device 10, e.g. the external slant angle may be chosen such that the medical device 10 has a smooth edge to prevent perforation or damage of the blood vessel wall, whereas the slanted angle of the ultrasound transducer 51 may be larger, e.g. closer to 90°.

Figure 8:
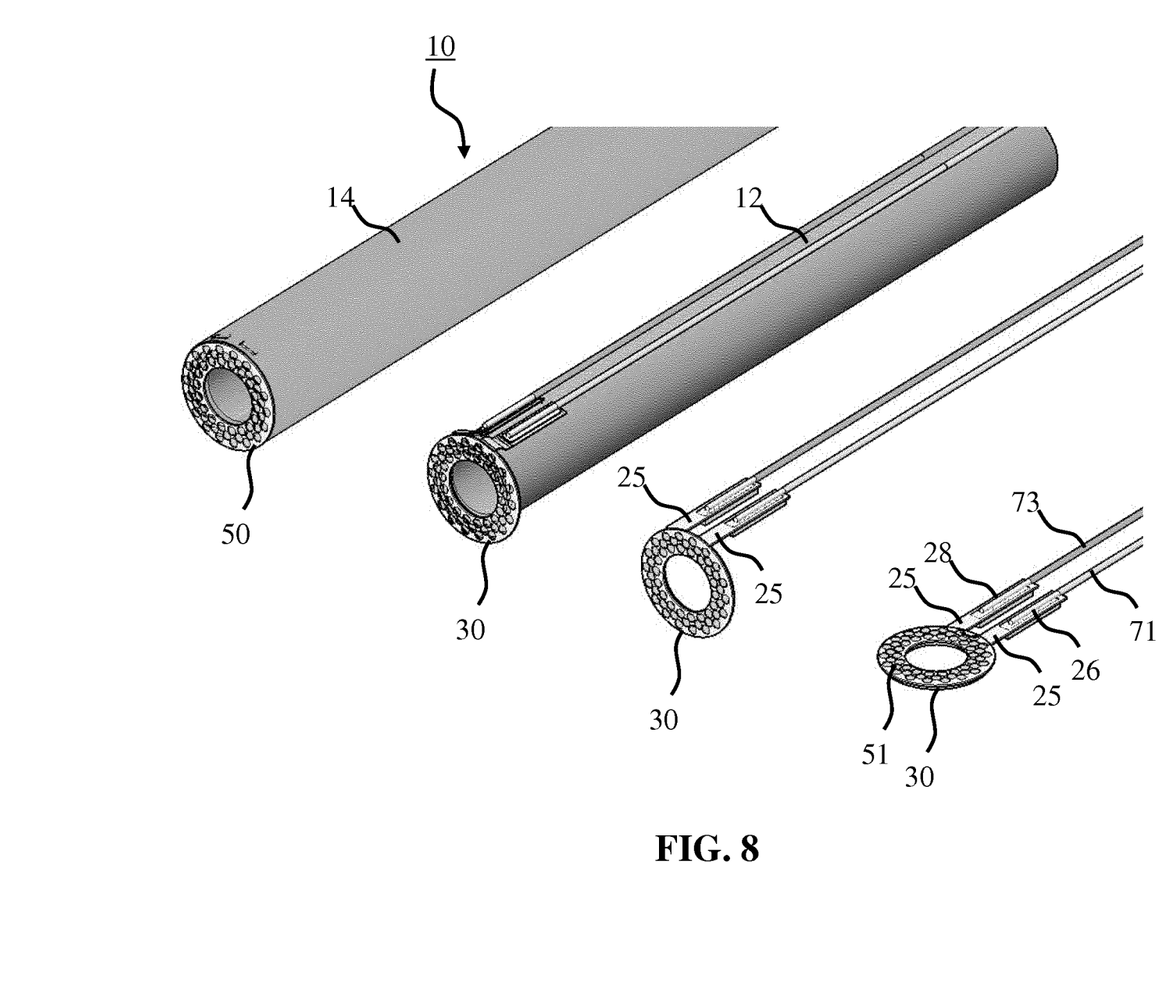
FIG. 8 schematically depicts an assembly method for another carrier onto a medical device according to an embodiment.

FIG. 8 schematically depicts another embodiment of the medical device 10 in which the ultrasound transducer arrangement 50 is provided using flex-to-rigid technology. In this embodiment, a rigid annular carrier 30 such as a silicon carrier carrying the ultrasound transducer arrangement 50, i.e. one or more ultrasound transducer elements 51, is flexibly connected to the contacts 26, 28 through flexible hinges 25, e.g. polyimide hinges or the like through which the conductive connections from the contacts 26, 28 to the one or more ultrasound transducer elements 51 extend as previously explained. As before, the ultrasound transducer elements 51 may be any suitable type in this embodiment. The flexible hinges 25 allow for the contacts 26, 28 to be positioned on the lumen body 12 as previously described whilst the rigid annular carrier 30 is folded onto the forward facing edge 13 of the lumen body 12 after which the outer surface or sheath 14 may be formed over the lumen body 12 to finalize the medical device 10 such that the wires 71, 73 run in between the lumen body 12 and the outer surface 14 in a length direction of the medical device 10 as previously explained.

It is reiterated that two contacts 26, 28 and two wires 71, 73 are shown by way of non-limiting example only as any suitable number of contacts and wires may be positioned onto the lumen body 12. For example, in embodiments in which the ultrasound transducer elements 51 are individually addressable or are grouped into individually addressable groups of ultrasound transducer elements 51, each individually addressable element group may be connected to a separate wire via a separate contact as will be readily understood by the skilled person.

Figure 9:
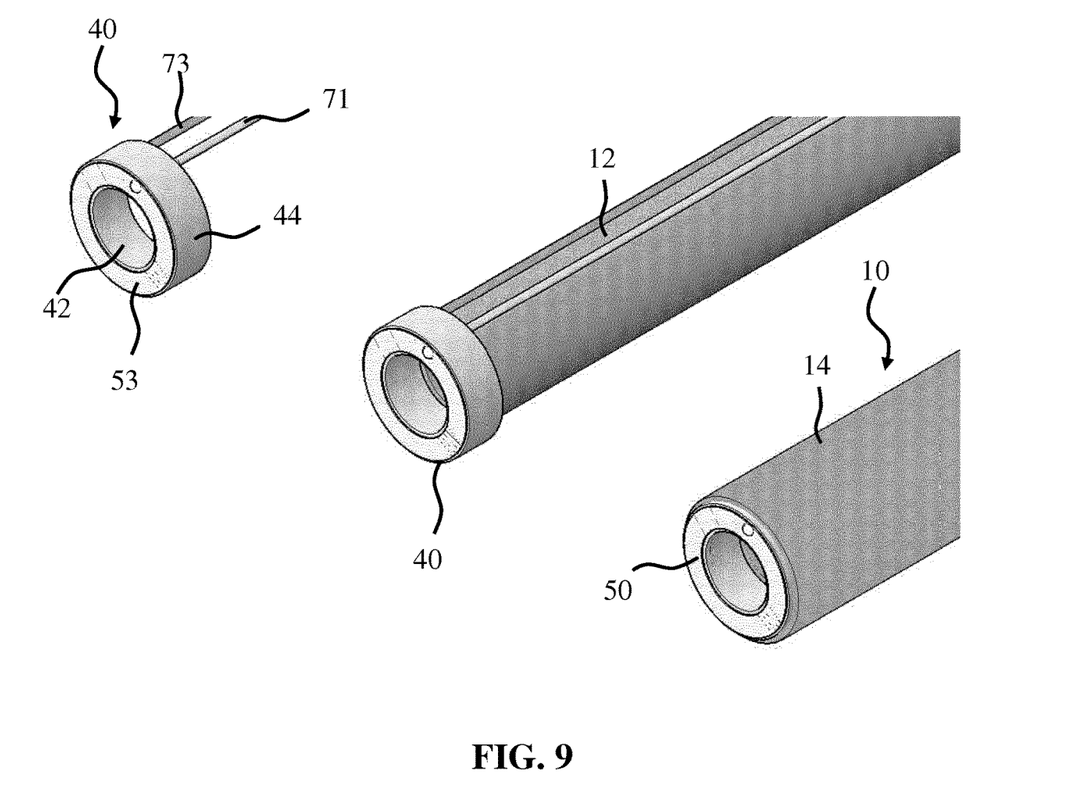
FIG. 9 schematically depicts an assembly method for yet another carrier onto a medical device according to an embodiment.

FIG. 9 schematically depicts an embodiment of the medical device 10 in which the ultrasound transducer arrangement 50 is formed by an annular substrate 53 including one or more of the ultrasound transducer elements 51, which annular substrate 53 is housed in the carrier 40, i.e. in an annular housing having an annular inner wall 42 aligning with the lumen 15 and an annular outer wall 44 in between which the annular substrate 53 is housed. In this embodiment, the annular substrate 53 may comprise one or more PZT elements for example. The annular substrate 53 may further comprise a number of contacts, e.g. at the backside of the annular substrate 53 to which one or more wires 71, 73 may be connected to facilitate communication between the ultrasound transducer arrangement 50 and a control unit (not shown) connected to the medical device 10. Alternatively, such contacts may be provided to the housing 40, with the housing further comprising internal conductive path between such contacts and the one or more ultrasound transducer elements of the ultrasound transducer arrangement 50 on the annular substrate 53.

At least the outer wall 44 of the housing or carrier 40 is dimensioned such that the lumen body 12 can be fitted within the outer wall 44, i.e. the outer wall 44 of the carrier 40 may tightly fit around the lumen body 12. An adhesive or the like may further be applied between the outer wall and the lumen body 12 or any other suitable securing means may be used to secure the carrier 40 to the lumen body 12 if necessary. Once the annular carrier 40 is fitted at the distal tip of the medical device 10, the outer surface or sheath 14 is formed over the lumen body 12 as previously explained to finalize the medical device 10 such that the one or more wires 71, 73 extend in a length direction of the medical device 10 in between the lumen body 12 and its outer surface 14.

Figure 10:
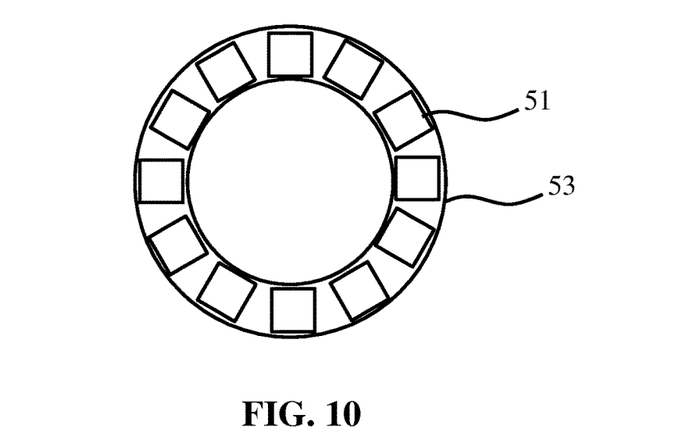
FIG. 10 schematically depicts a front view of a further carrier for mounting onto a medical device according to an embodiment.

The entire forward facing annular surface of the annular substrate 53 may act as a single ultrasound transducer, such as a PZT ultrasound transducer. Alternatively, as schematically depicted in FIG. 10, the forward facing annular surface of the annular substrate 53 may be segmented into a plurality of such PZT ultrasound transducer elements 51 or individually diced single crystal ultrasound transducer elements 51, in which case the respective PZT or single crystal ultrasound transducer elements 51 may be interconnected by a common electrode, for example when the PZT ultrasound transducer elements 51 are to be operated simultaneously. Other suitable (electrode) arrangements will be immediately apparent to the skilled person.

Figure 11:
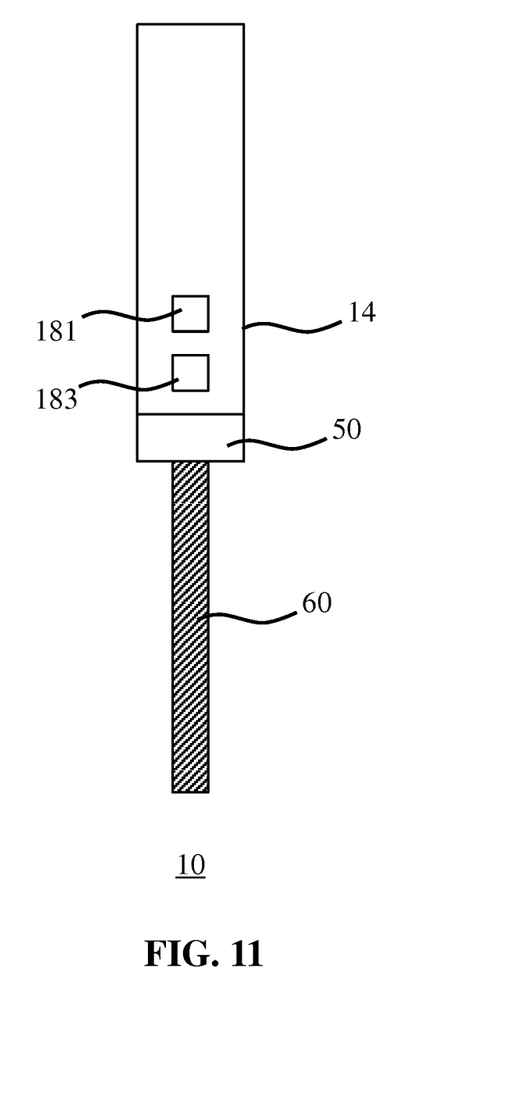
FIG. 11 schematically depicts a cross-sectional view of an aspect of a minimally invasive medical device according to yet another example embodiment.

In addition to the forward facing ultrasound transducer arrangement 50 around the exit port of the lumen 15 at the distal tip of the medical device 10, the medical device 10 in some embodiments further comprises at least one of a pressure sensor 181 and an imaging element 183 on the outer surface 14 of the medical device 10 as schematically depicted in FIG. 11. In the context of the present application, it should be understood that where reference is made to the presence of such a pressure sensor 181 and/or an imaging element 183 on the outer surface 14, this is intended to include embodiments in which such a pressure sensor 181 and/or imaging element 183 are at least partially embedded in the outer surface 14 or at least partially obscured thereby. Such a pressure sensor 181 and/or imaging element 183 are preferably positioned at the distal portion of the medical device 10 in close proximity to the ultrasound transducer arrangement 50 such that data obtained with the various sensors relates to the same region of interest within the blood vessel 1 of the patient, e.g. to the same portion of the blood vessel 1.

The inclusion of one or more pressure sensors 181 on the outer surface of the medical device 10 enables the (simultaneous) determination of both blood pressure and blood flow velocity measurements, which for example facilitates the detection of localized narrowing in a region of interest of the blood vessel 1 of the patient in which the distal portion of the medical device 10 is located, as well as the quantification of the severity of such an anomaly. In addition, by updating both pressure (P) and velocity (V) signals the pulse wave velocity (PWV) may be determined as PWV~dP/ρdV, in which ρ is the blood density. The determination of the pulse wave velocity for example may be useful for patient stratification in renal denervation procedures. The inclusion of one or more image sensors 183 enables the inclusion of anatomical information together with the blood flow velocity and blood pressure measurements in case of the presence of one or more pressure sensors 181. Such anatomical information for example when combined with blood flow velocity data may assist in the computation of the absolute blood flow (ml/min) of the patient from which cardiac output of the patient may be determined. The one or more image sensors 183 may be any suitable type of image sensor, such as for example an ultrasound transducer (array) or an optical image sensor.

Table I below gives the results of computational fluid dynamics (CFD) simulation of blood flow measurements performed with a prior art medical device having an ultrasound transducer arrangement on the guidewire 60 as schematically depicted in FIG. 1 and a medical device 10 according to an embodiment of the present invention comprising an annular ultrasound transducer arrangement 50 around the exit port of the lumen 15 at the distal tip of the medical device 10, here a micro-catheter.

TABLE I

|  | Volumetric blood flow (ml/min) | $V_{max}$ (m/s; prior art device) | $V_{max}$ (m/s, invention) |
|---|---|---|---|
|  | 50 | 0.20 | 0.17 |
|  | 150 | 0.52 | 0.49 |
| CFR | 3.0 (reference) | 2.6 | 2.9 |

The CFD simulations demonstrate that the positioning of the ultrasound transducer arrangement 50 on the distal tip of the medical device 10 instead of on the guidewire 60 does not significantly affect the peak blood flow velocity ($V_{max}$) measurement in a typical sample area of 5 mm from the ultrasound transducer(s), whilst a marked improvement in the determination of the coronary flow reserve (CFR) is achieved. This can be explained by the fact that a larger number of ultrasound transducers may be fitted onto the distal tip of the medical device 10, thereby increasing acoustic field intensity and improving signal to noise ratios.

Figure 12:
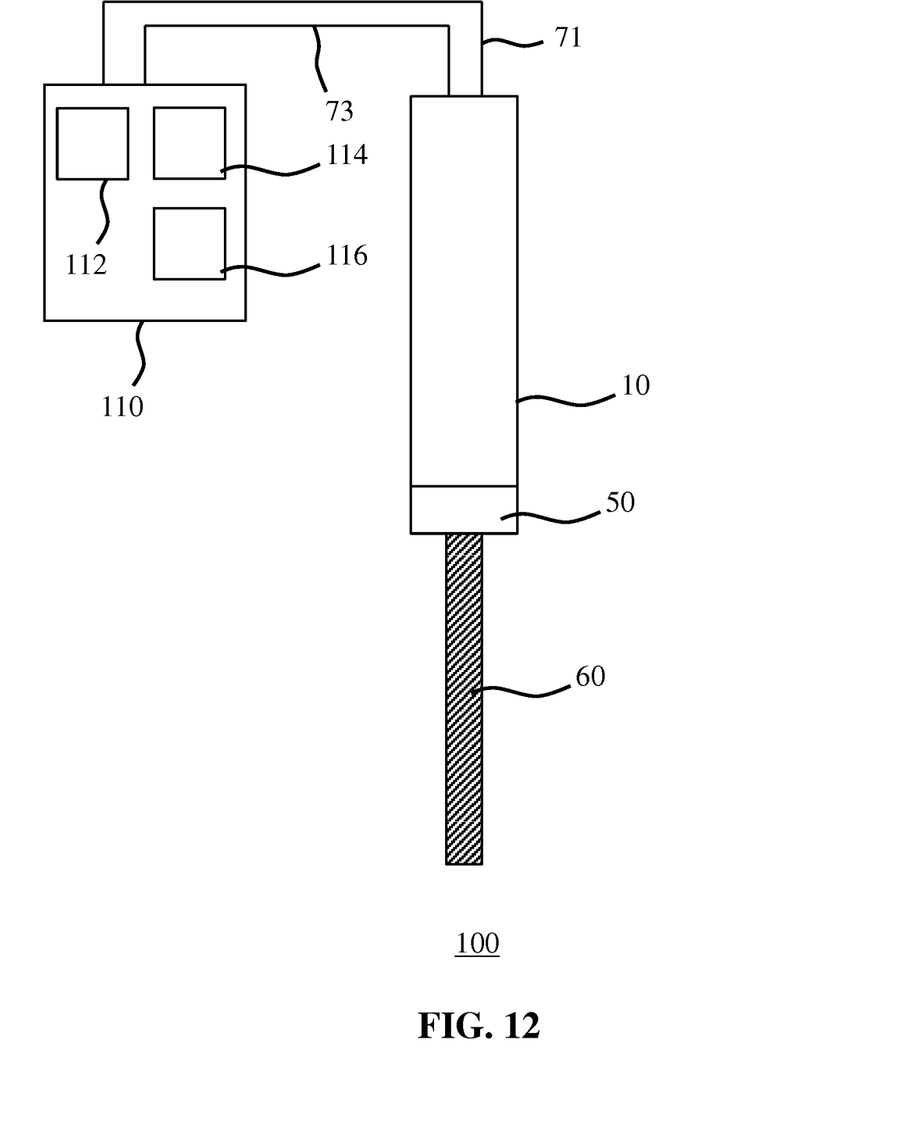
FIG. 12 schematically depicts a system including a minimally invasive medical device according to an embodiment.

FIG. 12 schematically depicts a system 100 including a control unit 110 such as a user console or the like communicatively coupled to the medical device 10 through the one or more wires 71, 73. Such communication may be based on electrical signals or alternatively electro-optical signals such as disclosed in US 2015/0335231 A1 may be used for such communication. It is noted for the avoidance of doubt that FIG. 12 should not be interpreted such as to show that the one or more wires 71, 73 necessarily extend beyond the medical device 10 to the control unit 110. It is of course equally feasible that the one or more wires 71, 73 terminate in a connector arrangement (not shown) at a proximal end of the medical device 10, with the control unit 110 being connected to the medical device 10 through a cable or the like terminating in a reciprocal connector arrangement that interfaces with the connector arrangement of the medical device 10. More generally, any suitable connection between the control unit 110 and the medical device 10 may be contemplated within the context of the system 100.

The control unit 110 may comprise a processor arrangement 112 comprising one or more processors arranged to control the ultrasound transducer arrangement 50 of the medical device 10, e.g. to electronically steer the ultrasound beam of the ultrasound transducer arrangement 50 in case of the ultrasound transducer arrangement 50 comprising individually addressable ultrasound transducer elements 51 or individually addressable groups of such ultrasound transducer elements 51. The processor arrangement 112 typically is further arranged to process the (ultrasound echo) signals obtained by the ultrasound transducer arrangement 50. The processor arrangement 112 typically is arranged to operate the ultrasound transducer arrangement 50 in Doppler mode such as a pulsed Doppler mode in which during a first time interval the ultrasound transducer arrangement 50 is operated in transmit mode during which an ultrasound beam is generated and transmitted into the blood vessel 1 of the patient after which during a second time interval the ultrasound transducer arrangement 50 is operated in receive mode to receive frequency-shifted echoes from the transmitted ultrasound beam, which frequency-shifted echoes are processed by the processor arrangement 112 in order to derive blood flow related parameters such as blood flow velocity from the received frequency-shifted ultrasound echo signals, e.g. from the magnitude of the frequency shift as is well-known per se.

Alternatively, the processor arrangement 112 is arranged to operate the ultrasound transducer arrangement 50 in a continuous wave Doppler mode in which a first set of ultrasound transducer elements 51 is operated in a transmit mode whilst a second set of ultrasound transducer elements 51 is simultaneously operated in a receive mode. This requires that both sets are individually addressable as will be understood by the skilled person. It is noted for the sake of completeness that continuous wave Doppler typically does not allow the determination of the blood flow velocity at a specific depth, i.e. a specific distance from the ultrasound transducer arrangement 50, but instead measures blood velocities along the entire line of interrogation. This is therefore less suitable in a scenario in which the user is interested in a localized blood flow related parameter, e.g. in the vicinity of an anomaly such as a stenosis, but has the advantage that much higher blood flow velocities may be determined, e.g. velocities of around 4 m/s, which for example may occur in a patient suffering from an aortic stenosis. In yet another embodiment, the processor arrangement 112 is arranged to switch the operation of the ultrasound transducer arrangement 50 between a pulsed Doppler mode and a continuous wave Doppler mode in order to obtain both localized blood flow related parameters, i.e. at a defined depth from the ultrasound transducer arrangement 50 as well as blood flow related parameters along the entire line of interrogation (depth of field) of the ultrasound transducer arrangement 50.

Where the ultrasound transducer arrangement 50 comprises a plurality of individually addressable ultrasound transducer elements 51, the processor arrangement 112 may implement an algorithm that derives the respective peak blood flow velocities from the frequency-shifted echoes obtained by each of the individually addressable ultrasound transducer elements 51 to determine the alignment of the medical device 10 with the blood vessel 1 of the patient. Based on the determined alignment of the medical device 10 with the blood vessel 1 of the patient, the processor arrangement 112 may generate a set of beam steering signals for the individually addressable ultrasound transducer elements 51 to improve the alignment of the field of view 52 of the ultrasound transducer arrangement 50 with the blood vessel 1, i.e. correct a misalignment of this field of view 52 with the blood vessel 1 through electronic beam steering.

The control unit 110 may further comprise a first user interface device 114, such as monitor or display or the like onto which blood flow measurement results as well as other results, e.g. blood pressure measurements with blood pressure sensor(s) 181 and anatomical information obtained with image sensor(s) 183 are presented to a user, as is well-known per se. The control unit 110 may further comprise a second user interface device 116, such as a keyboard, mouse, trackball and so on, or any combination of such user input devices, through which the user may control the operation of the medical device 10 and process the data acquired with the medical device 10 as is well known per se. The first user interface device 114 and the second user interface device 116 each may be integral to the control unit 110 or may be peripheral devices that are connected to the control unit 110 in a wired or wireless manner, e.g. using Bluetooth or the like. The first user interface device 114 and the second user interface device 116 may be integrated into a single user interface device, such as for example a touchscreen. Many other variations of the embodiments of such a control unit 110 will be immediately apparent to the skilled person, and it should be understood that the aforementioned description of the control unit 110 is by way of non-limiting example only. Any suitable control unit 110 for use with a medical device 10 according to embodiments of the present invention may be contemplated.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. Interventional medical device, comprising:
   an elongate body comprising:
      a longitudinal axis;
      a forward-facing surface at a distal end of the elongate body;
      a side-facing surface; and
      an edge located where the side-facing surface and the forward-facing surface join; and
   a sensor arrangement disposed at the distal end of the elongate body such that the sensor arrangement is distinct from the elongate body, wherein the sensor arrangement comprises:
      a carrier coupled to the forward-facing surface, the edge, and the side-facing surface of the elongate body, wherein the carrier comprises:
         a first side;
         an opposite second side;
         a proximal portion; and
         a distal portion, wherein the distal portion of the carrier comprises a body segment, a finger segment distal of the body segment, and a middle segment between the body segment and the finger segment along the longitudinal axis;
      a first wafer portion formed on the body segment on the second side of the carrier;
      a second wafer portion formed on the finger segment on the second side of the carrier; and
      a sensor element provided in the second wafer portion and not in the first wafer portion,
   wherein the first wafer portion and the second wafer portion are spaced from one another along the longitudinal axis such that no material extends over the middle segment of the carrier;
   wherein the carrier is configured for electrical conduction of signals from the proximal portion of the carrier to the sensor element;
   wherein the middle segment of the carrier is positioned on the edge of the elongate body, wherein the finger segment of the carrier, the second wafer portion, and the sensor element are positioned on the forward-facing surface of the elongate body such that the sensor element and the forward-facing surface are distinct from one another; and
   wherein the body segment of the carrier and the first wafer portion are positioned on the side-facing surface of the elongate body.

2. The device of claim 1, wherein the elongate body comprises a through lumen.

3. The device of claim 1, further comprising a plurality of second wafer portions each comprising at least the sensor element, wherein the sensor elements of the plurality of second wafer portions form an annular array on the forward-facing surface of the elongate body.

4. The device of claim 1, wherein the distal end of the second wafer portion is tapered inwardly toward the distal end of the carrier.

5. The device of claim 1, wherein the forward-facing surface of the elongate body is slanted relative to the longitudinal axis.

6. The device of claim 1, wherein the sensor element is a micromachined sensor.

7. The device of claim 1, wherein the sensor element is at least one of: an ultrasound sensor, a pressure sensor, or a flow sensor.

8. The device of claim 1, wherein the carrier is partially covered by an outer sheath in a longitudinal direction of the device.

9. The device of claim 8, wherein the proximal portion of the carrier is configured to receive and transmit signals to a control unit, and wherein the proximal portion of the carrier is covered by the outer sheath.

10. The device of claim 8, wherein the outer sheath of the device further comprises at least one of a pressure sensor or an imaging sensor, exposed to a surrounding environment through the outer sheath.

11. The device of claim 1, wherein the second side of the carrier is attached to the elongate body.

12. The device of claim 11, wherein the second side of the carrier is attached to the elongate body via the array of separate elongate wafer portions.

13. The device of claim 1, wherein the sensor element is positioned on the first side of the finger segment.

14. A system comprising:
   the interventional medical device of claim 1; and a control unit adapted to control the sensor element of the interventional medical device.

15. The system of claim 14, wherein the sensor element comprises an individually addressable ultrasound transducer element, and wherein the control unit is adapted to:
   determine a peak blood flow velocity from ultrasound data obtained with said ultrasound transducer element; and
   electronically steer an ultrasound beam produced by the ultrasound transducer element based on the determined peak blood flow velocities.

16. A method of manufacturing an interventional medical device, comprising:
   providing an elongate body comprising:
      a longitudinal axis;
      a forward-facing surface at a distal end of the elongate body;
      a side-facing surface; and
      an edge located where the side-facing surface and the forward-facing surface join;
   providing a sensor arrangement distinct from the elongate body and comprising:
      a carrier comprising:
         a first side;
         an opposite second side;
         a proximal portion; and
         a distal portion, wherein the distal portion of the carrier comprises a body segment, a finger segment distal of the body segment, and a middle segment between the body segment and the finger segment along the longitudinal axis;
   forming a first wafer portion on the body segment on the second side of the carrier and a second wafer portion on the finger segment on the second side of the carrier, wherein a sensor element is provided in the second wafer portion and not in the first wafer portion, wherein the first wafer portion and the second wafer portion are spaced from one another along the longitudinal axis such that no material extends over the middle segment of the carrier, and wherein the carrier is configured for electrical conduction of signals from the proximal portion of the carrier to the sensor element;
   positioning the middle segment of the carrier on the edge of the elongate body; and
   folding the finger segment of the carrier over the edge such that:
      the finger segment of the carrier, the second wafer portion, and the sensor element are positioned on the forward-facing surface of the elongate body such that the sensor element and the forward-facing surface are distinct from one another; and
      the body segment of the carrier and the first wafer portion are positioned on the side-facing surface of the elongate body.

* * * * *